United States Patent
Bonacci

(10) Patent No.: US 6,513,925 B1
(45) Date of Patent: Feb. 4, 2003

(54) SNUG FITTING FLOATING EYEGLASSES

(76) Inventor: Thomas A. Bonacci, 2047 Calvert Ave., Costa Mesa, CA (US) 92626

( * ) Notice: Subject to any disclaimer, the term of this patent is extended or adjusted under 35 U.S.C. 154(b) by 0 days.

(21) Appl. No.: 10/133,281

(22) Filed: Apr. 29, 2002

(51) Int. Cl.[7] .................................................. G02C 1/00
(52) U.S. Cl. ........................................ 351/43; 351/62
(58) Field of Search .............................. 351/43, 62, 41, 351/158, 111, 121, 156

(56) References Cited

U.S. PATENT DOCUMENTS

| D299,034 S | 12/1988 | Seaboyer |
| 4,877,320 A | * 10/1989 | Holden .......................... 351/44 |
| 4,934,807 A | 6/1990 | Boll'e et al. |
| D336,098 S | 6/1993 | Evans |
| 5,319,396 A | 6/1994 | Cesarczyk |
| D362,011 S | 9/1995 | Kolertsi |
| 5,488,441 A | 1/1996 | Pomatti |
| 5,495,303 A | 2/1996 | Kolentsi |
| 6,059,408 A | 5/2000 | Bonacci |

* cited by examiner

Primary Examiner—Hung Xuan Dang
(74) Attorney, Agent, or Firm—Gordon K. Anderson

(57) ABSTRACT

The floating eyewear of the invention fits eyeglasses fit snugly to a wearers head and consists of a frame (20) with bridge (24) in the middle and a pair of lenses (22), one on each side of the bridge. A pair of side temples (30) each have at a pair of openings (44) therethrough, with the temples inside surface configured with a flat portion (40) and a raised edge (42) that protectively encompasses the flat portion. The outside surface (38) is in a convex outer shape. Hinges connect the temples to the frame permitting them to be folded flat against the frame for ease of handling and storage. A pair of float pads (54) are configured in a recessed inverse image of the opening through each side temple and each float pad is snapped into forced into conformance with the temple opening securing it in place due to the flexibility of the pad. The pads engagement with a wearers head creates a snug fit and the pads buoyancy is sufficient to overcome the combined weight of the frame and temples permitting the eyewear to float in water with the temples protruding vertically above waters surface.

20 Claims, 5 Drawing Sheets

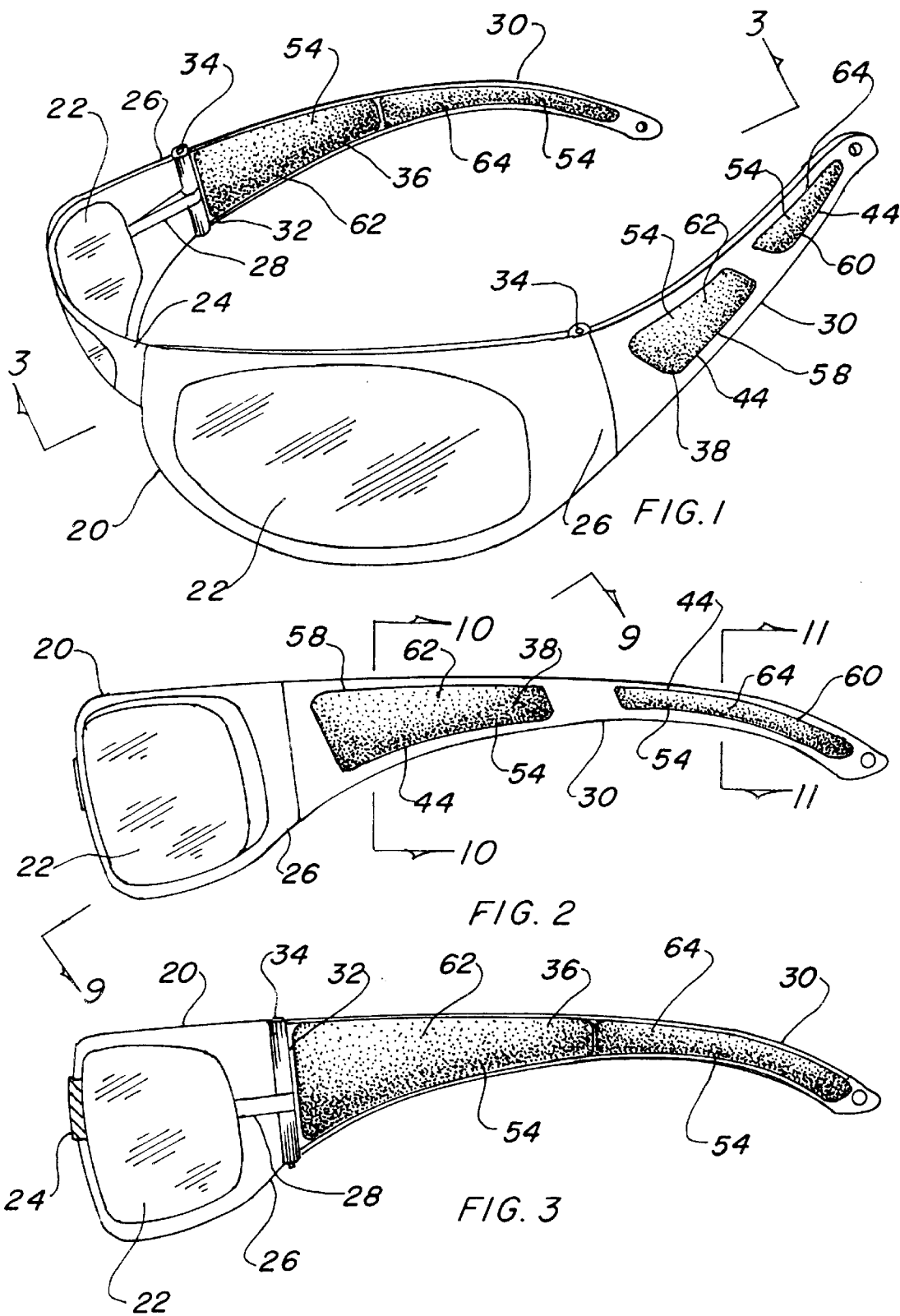

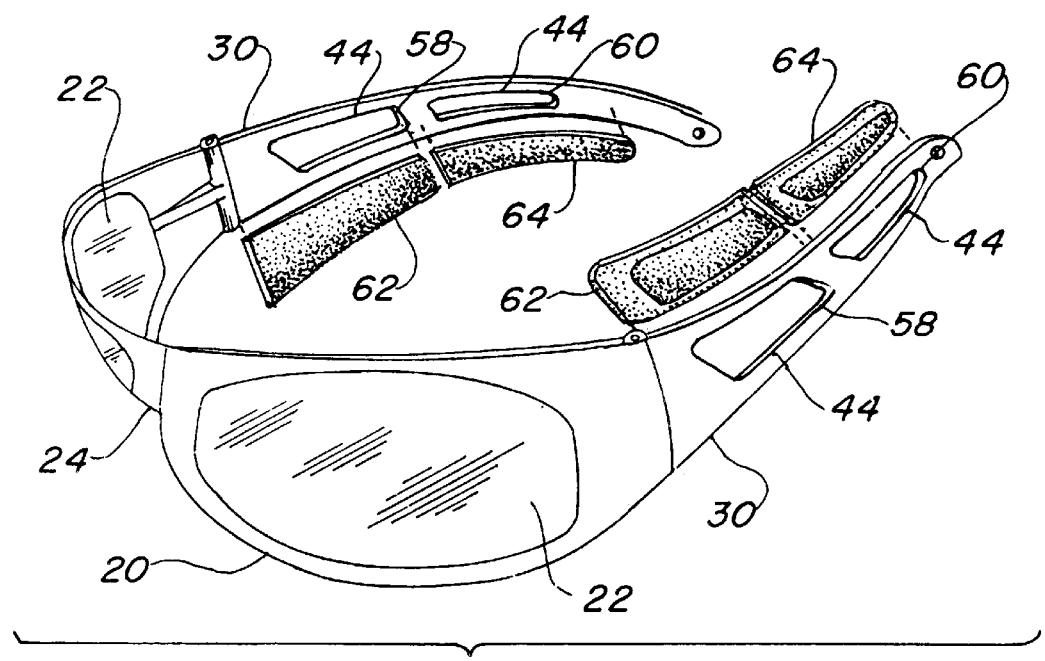
FIG. 20
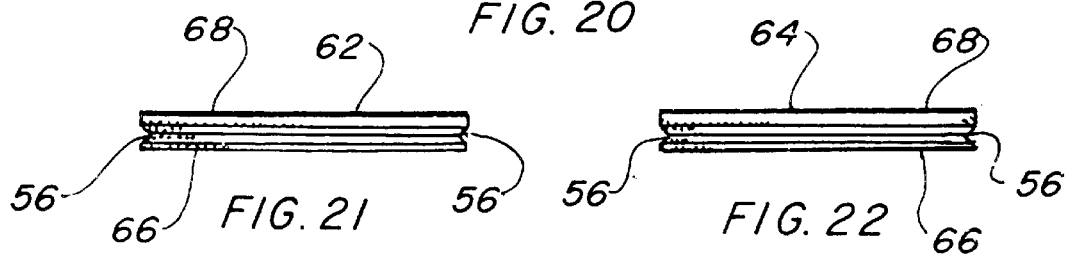
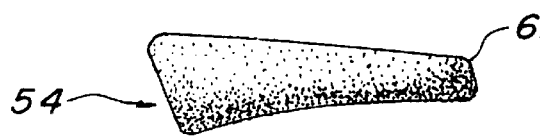
FIG. 23
FIG. 24
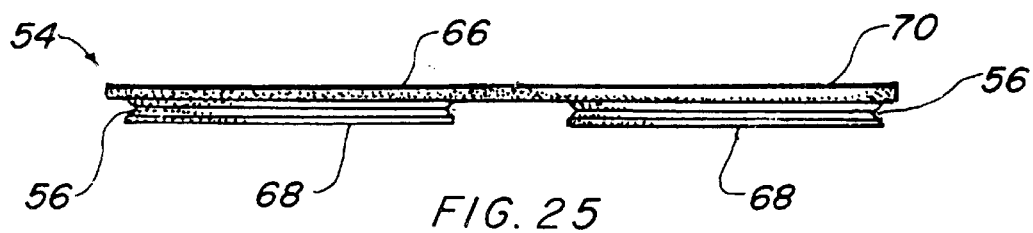
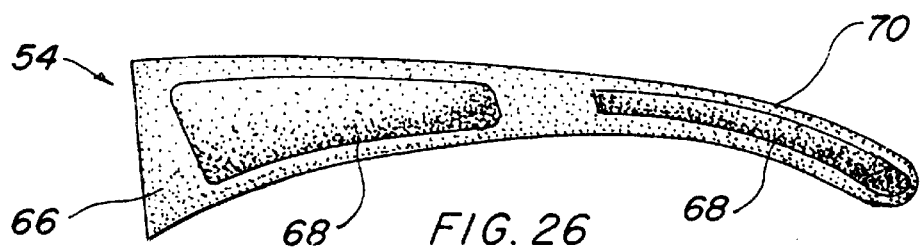

SNUG FITTING FLOATING EYEGLASSES

TECHNICAL FIELD

The present invention relates to eye wear in general. More specifically to sunglasses, safety glasses and clear lens glasses that fit tightly and float in water.

BACKGROUND ART

Previously, many types of sunglasses or devices to hold sunglasses have been developed in endeavoring to provide an effective means to prevent loss in the water. Prior art has employed adding a material to the glasses having a specific gravity of less than one when combined with the eyeglasses allowing them to float. In most cases, material has been added to the frame along the brow either permanently or in a removable manner to accommodate these desired characteristics. Others have simply employed devices that attach to conventional glasses, either to the ends of the temples or completely encase the glasses with a floatable material.

A search of the prior art did not disclose any patents that read directly on the claims of the instant invention, however the following U.S. patents are considered related:

| U.S. Pat. No. | Inventor | Issue Date |
| --- | --- | --- |
| 6,059,408 | Bonacci | May 9, 2000 |
| 5,495,303 | Kolentsi | Feb. 27, 1996 |
| 5,488,441 | Pomatti | Jan. 30, 1996 |
| 5,319,396 | Cesarczyk | Jun. 7, 1994 |
| 4,934,807 | Boll'e et al. | Jun. 19, 1990 |
| Des.362,011 | Kolentsi | Sep. 5, 1995 |
| Des.336,098 | Evans | Jun. 1, 1993 |
| Des.299,034 | Seahoyer | Dec. 20, 1988 |

U.S. Pat. No. 6,059,408 is my previous invention to which the improvements are directed. The improvements include the omission of the frame float pads adjacent to the hinges that connect the frame to the temples and an entirely different approach to the attachment of the float pads to the temples is used. Instead of simply attaching the float pads on the temples inside surface, the temples include a pair of openings in which molded float pads, that incorporate a molded reverse image of the temple openings, are forced into conformance due to the resilience of the float pads. The attachment is much like a grommet connection in that the pads exterior rests on the temples outside surface and the pads interior substantiality covers the temples inside surface. Further the temples are configured to include a flat portion with an edge that protrudes above and protectively encompasses the flat portion which includes the resilient floating material. The volume of closed cell pad material is equivalent to, or even in excess of, my previous patent therefore the buoyancy characteristics are either the same or slightly improved.

Kolentsi in U.S. Pat. No. 5,495,303 teaches eyeglasses that float due to the addition of a foam member added into a flange integrally formed into the top transverse frame member. The frame forms the front face of the eyeglasses and is curved rearwardly following the curvature of a wearer's face. A single transparent or translucent convex lens is secured to the frame by being located in a slot present in the underside of the frame. A flange is formed on the interior side of the frame and a foam cushion/floatation strip is imbedded into the flange for attachment and to prevent natural loss of attaching adhesive on hot days. The buoyancy of the foam member is greater than the weight of the eyewear permitting the glasses to float.

U.S. Patent issued to Pomatti, U.S. Pat. No. 5,488,441 discloses an eyeglass frame arrangement that has a semi-rigid lens retaining support and a semi-flexible bridge and temples. A retaining strap engages the back of the users head and close cell padding surrounds the lenses such that the eyes of the user are protected from the elements. In another embodiment the eye pads are integrated with the lens support and are attached to the temple bows.

U.S. Pat. No. 5,319,396 issued to Cesarczyk is for eyeglasses and goggles that have a shield member attached to the frame, with the shield having tapered ends. A plastic foam member is configured to fit into a groove in the shield. During use this plastic member is held in place snugly against a wearers face on the brow to prevent perspiration from falling into ones eyes.

U.S. Pat. No. 4,934,807 issued to Boll'e et al. teaches sunglasses having a detachable absorber strip. The sunglasses utilized have a replaceable convex optically clear pane that is curved both horizontally and vertically. An absorber strip, utilizing a sponge material, is removably attached to the frame of the glasses and the glasses include interchangeable temple members for fit and comfort.

U.S. Pat. No. De. 362,011 of Kolentsi discloses the design of floating eyeglasses having the same appearance as the subsequent U.S. Pat. No. 5,494,303 issued to the same inventor at a later date.

U.S. Pat. No. Des. 336,098 of Evans is for the ornamental design of an eyeglass holder that is made of a material that floats in water with sufficient buoyancy to permit eyeglasses attached thereunto to also float.

Seaboyer in U.S. Pat. No. Des. 299,034 teaches the ornamental design of sunglasses formed with a single wrap around lens and apparently an adjustable head band with a elongated portion that circumvents the wearers head.

DISCLOSURE OF THE INVENTION

Eye wear of any type used for outdoor activities, particularly sun glasses that are worn in sports that include speed and accelerated movements, obviously become venerable to breakage and loss. This fact is particularly evident in water sports using engine powered equipment such as jet skis and power boats pulling water skiers where a fall easily leads to loosing ones glasses in the water due to the impact when falling. It is therefore a primary object of the invention to have eye protection that allows detection and subsequent recovery when an inevitable loss occurs. The invention utilizes float pads attached through the temples of a pair of wrap around polycarbonate glasses. The location and volume of the closed cell foam sponge pads not only permits the glasses to float but always in the same direction, which is with the lenses down and the temples prominently protruding in a upward position above the water. The glasses are balanced to right themselves when entering the water from any orientation which allows the wearer to look for a obvious pair of temples elevated in an upward direction.

An improvement over the inventors prior art is in order as his previous invention, described in the above section, has been notably popular permitting changes to be incorporated to ameliorate its usefulness, product life and production simplicity. As previously noted, the improvements in the preferred embodiment include the omission of the frame float pads in front of the hinges and replacement of the mass by larger pads on the temples. The second embodiment however incorporates the original frame float pads and becomes somewhat of a super floater. In either case a different approach to the attachment of the float pads to the temples is utilized. The temples now include a pair of openings in which molded float pads, are forced into conformance through the openings using the resilience of the float pads. The pads now incorporate a molded reverse image of the temple openings, and the attachment is like a grommet connection in that the pads exterior rests on the temples outside surface and the pads interior substantiality covers the temples inside surface. It may be clearly seen that no adhesive is necessary in the preferred embodiment which simplifies the installation, eliminates the adhesive that may be susceptible to deterioration and affords an almost permanent closure.

Further the temples are configured to include a flat portion with an edge that protrudes above and protectively encompasses the flat portion which includes the resilient floating material. The volume of closed cell pad material is equivalent to, or even in excess of, my previous invention, according to the embodiment, therefore the buoyancy characteristics are either the same or slightly improved.

An important object of the invention related to the ease of locating the glasses when lost in the water, in that the float pads may be made with a highly visible color which easily distinguished from the hue of the water. Further the temple float pads are interchangeable and may be manually removed by the owner and replaced with either a vivid hue for distinguishing it in the water or a color that matches or is in harmony with the frame and temples according to their use.

Another object of the invention is directed to the protective edge that surrounds the flat portion of the frame. The float pads are enclosed on the edge which safeguards the exposed edges from being pulled away from the flat portion and helps to hold them in place since no adhesive is required in the attachment method.

As with the inventors previous patent another object is that conventionally configured glasses are adversely effected by the wind. A tight fit is achieved with the improved invention as the protective edge is slightly lower than the resilient foam easily permitting the extending foam to conform to the contour of the users head eliminating the loss of the eye wear when wind or speed is encountered. Loss of glasses is particularly a concern when riding a motor vehicle such as a open automobile, boat, motorcycle and the like, when the rider or driver turns his or her head to look to the rear. In this circumstance the wind catches this vulnerable area and blows the glasses from the face. This is apparent by observing someone in this type of situation when the person actually holds the glasses in place with the finger or hand while turning to look to the rear.

Still another object of the invention relating to the location of the float pads, which is only on the temples in the preferred embodiment, or located on both the frame and temples in the second embodiment with either embodiment allowing sufficient space to remain to prevent or at least minimize fogging of the lenses. In glasses that touch both the forehead and cheeks, as in some prior art, a persons evaporating perspiration has a tendency to collect on the lenses fogging them to the extent that vision is impaired, particularly when the glasses are initially brought into use. It has been found that in comparing similar glasses, the float pads greatly ameliorate this phenomena as air is permitted to flow freely and circulate around the lenses, whereas prior art using sponge material on the brow or glasses that are tight fitting on top and bottom completely impede the air flow.

Yet another object of the invention is realized by increasing user comfort when wearing the improved eye glasses by the addition of resilient pads. The pads not only increase wearer comfort due to its pliant nature but also helps keep the glasses from sliding off of ones face. It may be noted that almost all eyeglasses have the tendency to slip down on the nose when the wearer is hot and perspiration is present however since the temples are completely covered with a material that conforms to the contour of the head and is essentially springy it permits a greater degree of permanence. Comfort is realized in not only outdoor usage but when the eyeglasses have clear lenses and are the safety type, as preferred in the invention, particularly the type ANSI.Z87.1 approved by the American National Standard Institute, factory workers find this added resiliency along with the advantages noted above are extremely beneficial to the user. When the glasses are temporarily removed from ones face and placed around the neck or on top of the head they are much easier to be retained for the same reasons.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is a partial isometric view of the preferred embodiment.

FIG. 2 is a left side view of the preferred embodiment.

FIG. 3 is a view taken along lines 3—3 of FIG. 1.

FIG. 20 is an exploded view of the preferred embodiment.

FIG. 21 is a top view of the front float pad completely removed from the invention for clarity.

FIG. 22 is a top view of the rear float pad completely removed from the invention for clarity.

FIG. 23 is a outside view of the front float pad completely removed from the invention for clarity.

FIG. 24 is a outside view of the rear float pad completely removed from the invention for clarity.

FIG. 25 is a top view of the unitary float pad completely removed from the invention for clarity.

FIG. 26 is a outside view of the unitary float pad completely removed from the invention for clarity.

BEST MODE FOR CARRYING OUT THE INVENTION

Figure 4:
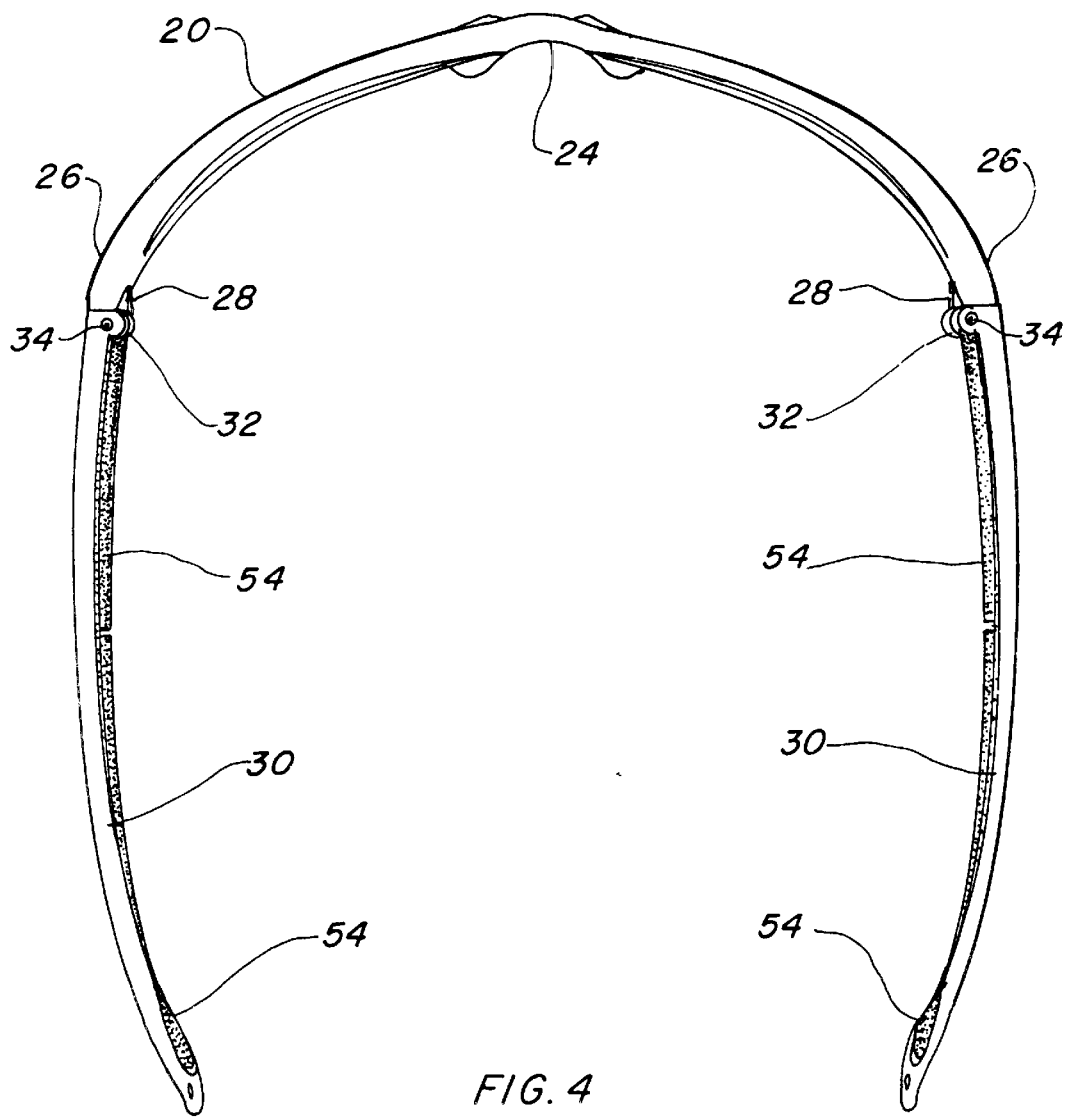
FIG. 4 is a top view of the preferred embodiment.
Figure 5:
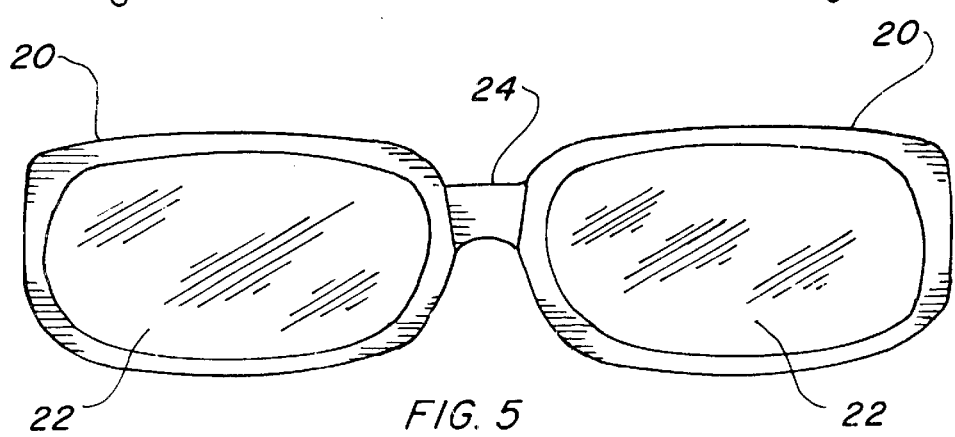
FIG. 5 is a front view of the preferred embodiment.
Figure 6:
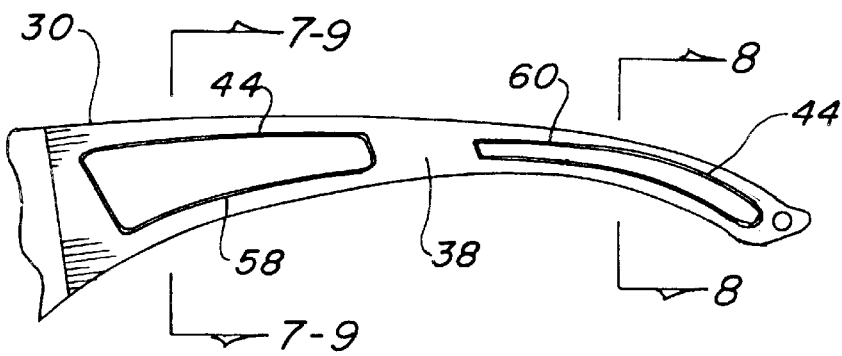
FIG. 6 is a left side view of the inside surface of the eyeglass temple less the float pads illustrating the openings in the side formed to attach the temple float pads through the openings in the frame.
Figure 7:
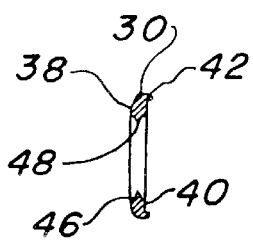
FIG. 7 is a cross sectional view taken along lines 7—7 of FIG. 6 illustrating temple opening perimeter in the sharp edge configuration.
Figure 8:
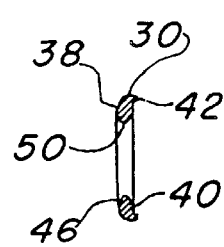
FIG. 8 is a cross sectional view taken along lines 8—8 of FIG. 6 illustrating temple opening perimeter in the half-spherical edge configuration.
Figure 9:
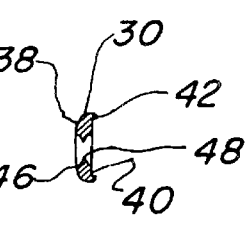
FIG. 9 is a cross sectional view taken along lines 9—9 of FIG. 6 illustrating temple opening perimeter in the square edge configuration.
Figure 10:
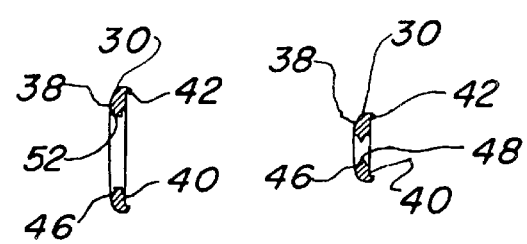
FIG. 10 is a cross sectional view taken along lines 10—10 of FIG. 6.

The best mode for carrying out the invention is presented in terms of a preferred and a second embodiment. The preferred embodiment is shown in FIGS. 1 through 20 with slight variations illustrated in FIGS. 21 through 26. The preferred embodiment of the is comprised of an eyeglass frame 20 that includes and a middle bridge 24 across the top with ends 26 on each outside edge and a pair of lenses 22, one on each side of the bridge 24. Each of the frame ends 26 include means to hinge each side temple to the frame permitting the side temples 30 to be folded flat against the frame for ease of handling and storage. This hinge means is in the form of a single gusseted knuckle 28 integrally formed with the frame 20 adjacent to each end 26. A pair of side temples 30, each having a plurality of integrally formed aligned temple hinge knuckles 32, engage each single gusseted knuckle 28 therebetween. The temple hinge, knuckles 32 therefore align on either side of the gusseted knuckle 28 forming a continuous hinge. The temples 30 have a interfacing width equal to the width of the bridge ends 26 permitting the glasses to have a uninterrupted breadth from the frame to the temples as shown in FIGS. 1 and 2.

The side temples 30 are connected to the frame 20, each with a hinge pin 34, well known in the art, permitting the temples to pivot inwardly for storage when not in use. The eyeglasses are the so-called wrap-around type with the frame 20 covering a wearers brow, cheekbone and a portion of the ones temples. The glasses may be made of optically clear polycarbonate thermoplastic with the lenses 22 integrally formed with the frame 20, or the frame 20 and temples 30 may be opaque with the lenses 22 transparent. The frame 20 and temples 30 are preferably black in color with the lenses 22 colored to suit the intended usage. As an example for water and snow sports the lenses 22 are tinted a dark color, shooting glasses are normally yellow with safety glasses transparent. Other colors may include brown, amber, green, blue, gray and mirror etc. It is also best to include ultra violet ray protection with the lenses fabricated to meet government and industry standards including ANSI/FDA relative to their ability to absorb harmful rays. The lenses may also be polarized, if desired, to further reduce glare and reduce infiltrating light. It has been found that the clear lenses easily passed the tests that allowed approval by a government recognized agency for use as safety glasses.

It will be noted that the eye glasses thus described are basically the same in structure as conventional eyeglasses however in order for them to receive suitable floatation elements the temples 30 are inwardly curved, as illustrated in FIG. 3 in a smooth convex radial manner on the side next to the wearer. Preferably the thickness of the temples 30 is substantially uniform throughout as shown best in FIGS. 7–10.

The pair of side temples 30, each include an inside surface 36 and an outside surface 38, with the inside surface configured with a flat portion 40 and an raised edge 42 that protectively encompasses the flat portion 40 as shown in the cross section of FIGS. 7–13. The outside surface 38 has an essentially convex outer shape, and each temple 30 include at least one opening 44 therethrough. The opening 44 incorporates an internal perimeter 46 in either a sharp edge configuration 48, shown in FIGS. 7 and 10–13, a half spherical edge 50 configuration, shown in FIG. 8 or a square edge 52 configuration, shown in FIG. 9. It should be noted that the edge configuration may be in any convenient shape and still fall within the scope of this invention as the utility is the same.

Figure 11:
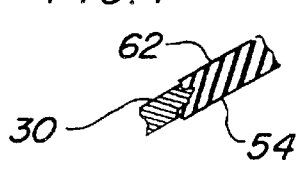
FIG. 11 is a cross sectional view taken along lines 11—11 of FIG. 2.
Figure 12:
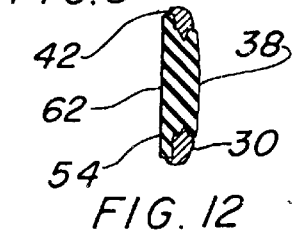
FIG. 12 is a cross sectional view taken along lines 12—12 of FIG. 2
Figure 13:
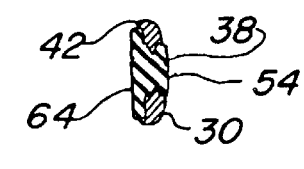
FIG. 13 is a cross sectional view taken along lines 13—13 of FIG. 2.
Figure 14:
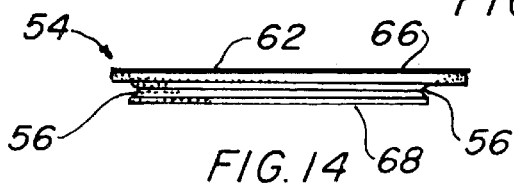
FIG. 14 is a top view of the front float pad completely removed from the invention for clarity.
Figure 15:
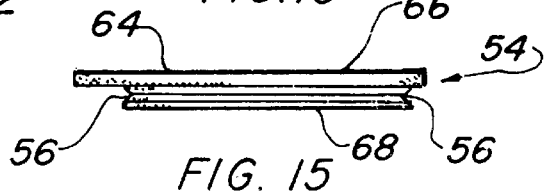
FIG. 15 is a top view of the rear float pad completely removed from the invention for clarity.
Figure 16:
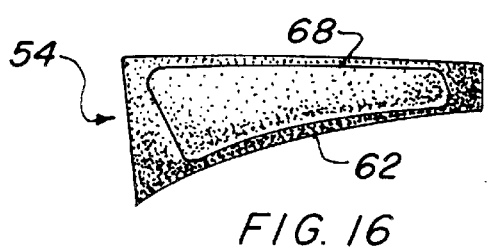
FIG. 16 is a outside view of the front float pad completely removed from the invention for clarity.
Figure 17:
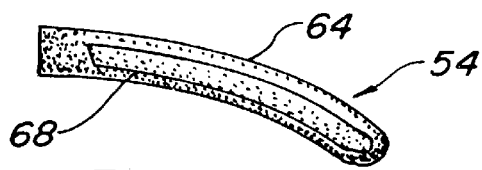
FIG. 17 is a outside view of the rear float pad completely removed from the invention for clarity.
Figure 18:
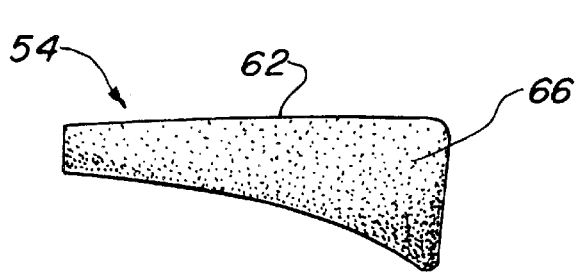
FIG. 18 is an inside view of the front frame float pad completely removed from the invention for clarity.
Figure 19:
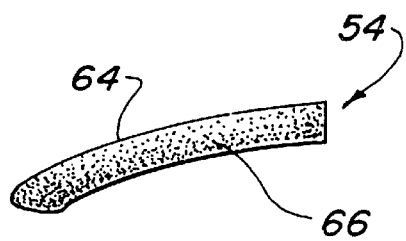
FIG. 19 is an inside view of the rear float pad completely removed from the invention for clarity.

In order to permit the eyewear to float in water at least one resilient float pad 54 in each temple 30, is configured in a reversed image of the opening 44 through each side temple 30, and is forced into conformance with the temple opening 44 securing the pad 54 in place utilizing the pads inherent flexibility. The float pads 54 incorporate an integral groove 56 along a longitudinal axis, with a molded edge in reverse image of the edge of each temple opening 44. Each pad 54 contiguously engages both the flat portion 40 of the inside surface 36 of each temple 30 on one side and the temples outside surface 38 on the other, in a grommet like manner as depicted in FIGS. 11–13. It should also be noted that the pad interior surface 66 protrudes slightly above the raised edge 42 in order to allow the pad 54 to compress slightly to conform to the users head for the snug fit and to retain them when worn. The protrusion is preferably at least one millimeter in height however it is not limited to this dimension.

The openings 44 are described as being at least one in each temple 30 as the number and configuration may change according to the application and to give the eyewear a pleasing appearance. Further the configuration of the opening 44 may be almost any shape as long as sufficient material remains in the temple 30 to assure the structural integrity of the framework. The shape may be round, square, oval, oblong, polygonal or any irregular configuration that meets the need. It will be noted that the shape of the opening 44 as shown in the drawings follows the temples outer edge and the ends are slanted or rounded to correspond and accentuate the shape of the temple 30.

In the preferred embodiment there are two openings 44 in each temple 30 which may be defined as a front aperture 58 and a rear aperture 60. Likewise there is a front float pad 62 and a rear float pad 64 with each pad having an interior surface 66 that contiguously engages the temples flat portion 40 of the inside surface 36. The pads exterior surface 68 contiguously engages the temples outside surface 38 adjacent to the opening 44, when both pads 62 and 64 are installed into the temples 30, as illustrated in FIGS. 1–3 and 14–19.

FIGS. 21–24 illustrate another embodiment in which the front 62 and rear 64 pad are configured slightly different in that the pad interior surface 66 is the same size as the exterior surface 68 and therefore each pads interior surface 66 contiguously engages only the temples inside flat portion 40 adjacent to each opening 44 in the temple 30. The pads exterior surface 68 contiguously engages the temples outside surface 38, adjacent to each opening 44 as above.

Yet another configuration of the float pads 54 is shown in FIGS. 25 and 26 which function in the same manner as the preferred embodiment except instead of being separate pieces it is molded in one piece as a unitary float pad 70. Again the configuration of the float pads 54 may be adjusted to accommodate the openings 44 in any of there forms as discussed above.

In any event the frame float pads 54 are made of closed cell foam sponge preferably of ethylene vinyl acetate material having a density of from 11 pounds per cubic foot (176.2 kilograms per cubic meter) to 13 pounds per cubic foot (208.2 kilograms per cubic meter), with 12 pounds per cubic foot (192.2 kilograms per cubic meter) preferred. The pads 54 may have a thickness of from 4 millimeters to 7 millimeters however it has been found that a thickness of either 5 or 6 millimeters is optimum for achieving the best floatation effect.

While the configuration of the pads are depicted in a very specific manner in the drawings for the wrap around type eye wear, other shapes function equally well on different styles of frames as long as sufficient area is available.

The color of the temple float pads 54 is important in that it leads to identification when in the glasses are in the water, therefore the pads may be a bright visual color integrally molded therein so as to be easily discernible when the eyewear is floating in water. For supplementary visualization it is possible to have a white background with a contrasting dark, preferably black, marble effect which is easily identified as it differs in not only color but in contrast. Further any single color, combination of colors or design may be equally well utilized in the invention as an example, a marbled fluorescent pink and purple or any emergency color such as fluorescent yellow, red etc. even a uniform design like stripes, dots, checks, repetitive individual figures or almost any design arrangement and combination may be acceptable.

The pads 54 color may also match the floating eyewear frame 20 and temples 30 for perceptible continuity. It may also be advantageous to have the manufacturers name, trade name or trademark such as "Bomber" or the like imprinted in raised or recessed indicia on the pads exterior surface 68 in the form of a mark or simply a name preferably on the front float pad 62. The pad interior surface 66 of the temple float pads may also optionally include a textured surface contiguous with a wearer for creating a non-slip grip.

The pads 54 engagement with a wearers head creates a snug fit and the pads 54 create sufficient buoyancy to overcome combined weight of the frame 20 and temples 30 permitting the eyewear to float in water with the temples 30 protruding vertically above waters surface.

Figure 27:
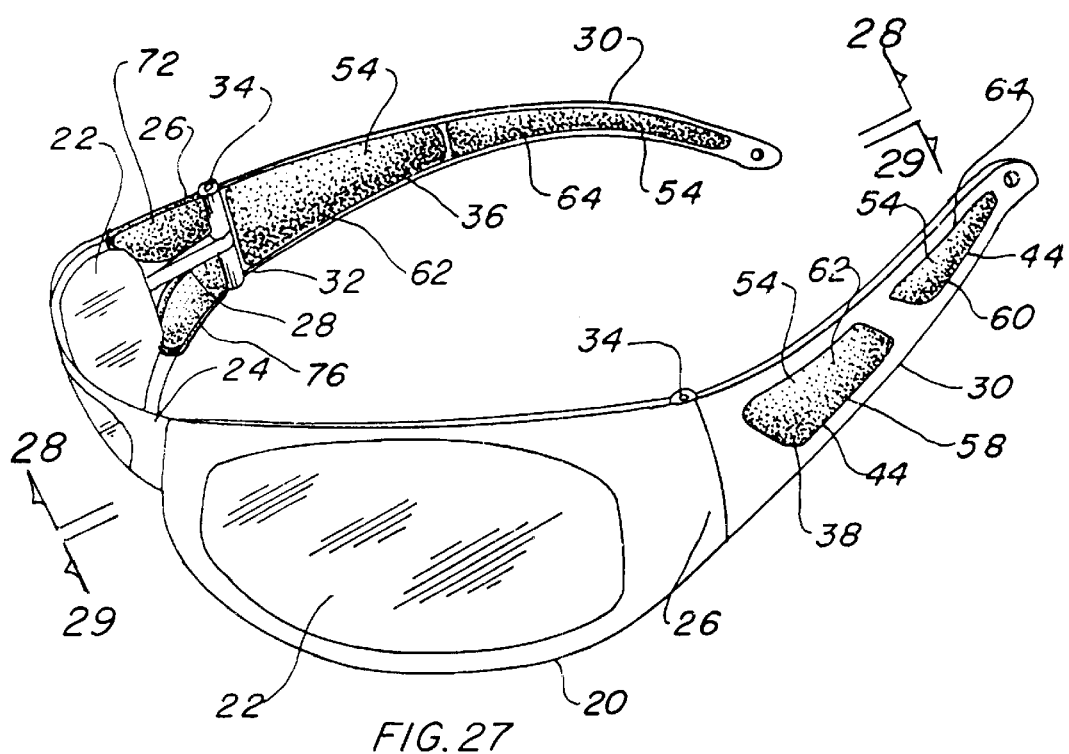
FIG. 27 is a partial isometric view of the second embodiment.
Figure 28:
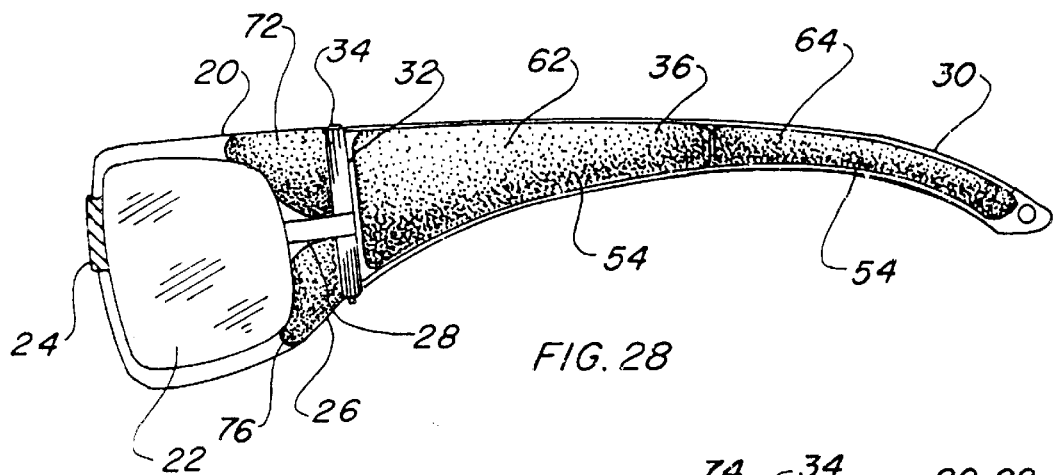
FIG. 28 is a view taken along lines 28—28 of FIG. 27.
Figure 29:
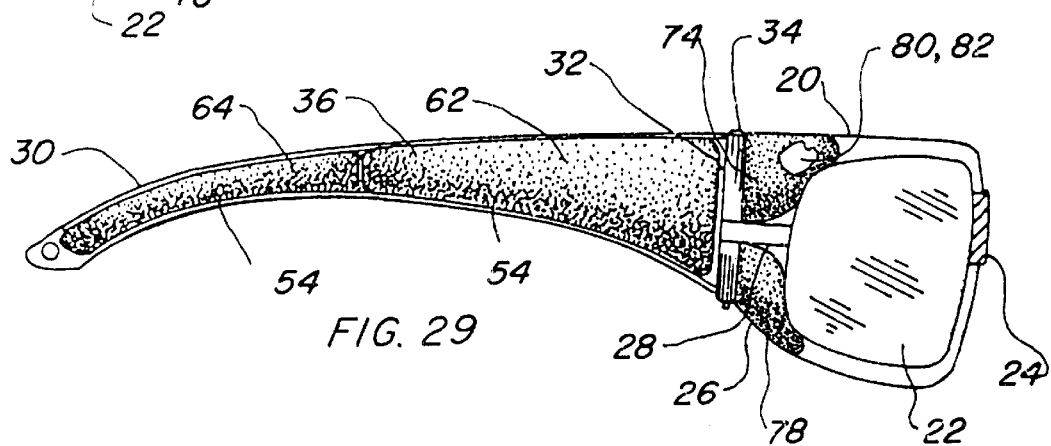
FIG. 29 is a view taken along lines 29–20 of FIG. 27.

The second embodiment is illustrated in FIGS. 27–29 and contains all of the elements and function of the preferred embodiment coupled with an additional feature consisting of frame float pads that are attached the frame adjacent to the hinge means. The additional float pads 54 are best described as individually shaped members located at strategic positions on the frame 20 adjacent to but not covering the lenses. A top right frame float pad 72 and a top left frame float pad 74 are in mirror images of each other. A bottom right frame float pad 76 and a bottom left frame float pad 78 complete the set and are likewise in mirror images of one another. Each of the frame pads are attached to the frame 20 in an area essentially adjacent to the frame ends 26 and both on top of and below the single gusseted knuckle 28 as illustrated in FIGS. 27–29. The frame float pads are made of closed cell foam sponge preferably of ethylene vinyl acetate material having a density of from 11 pounds per cubic foot (176.2 kilograms per cubic meter) to 13 pounds per cubic foot (208.2 kilograms per cubic meter), with 12 pounds per cubic foot (192.2 kilograms per cubic meter) preferred. The color is of little importance as the glasses float with the frame pads under the water however gray or black is a common color in this material.

The frame pads have a pressure sensitive backing 80 which is an acrylic based peel and stick adhesive however any other acceptable substance may be used with equal ease. The pads have a thickness of from 4 millimeters to 7 millimeters and it has been found that a thickness of either 5 or 6 millimeters is optimum for achieving the best floatation effect. The frame pads 72–78 may be optionally attached to the frame 20 with a contact cement 82 after the frame has been prepared with a priming solution to clean the surface of the frame and create a acceptable texture. Through experimentation it has been found that the 3M product Number 943M is ideal for cleaning and the cement is a Cemtrec product designated as Permagrip 56500 which functions exceptionally well for the application as it is impervious to water after curing. When united with the pressure sensitive backing the combination creates an almost permanent bond. Another method of attaching the frame pads 72–78 would be to include additional openings 44 in the frame and internal grooves 56 in the individual pads in a similar manner as the temple pads. The openings 44 may be round or any other shape and the grommet like closure would duplicate the temple pads attachment means.

While the invention has been described in complete detail and pictorially shown in the accompanying drawings, it is not to be limited to such details, since many changes and modifications may be made in the invention without departing from the spirit and scope thereof. Hence, it is described to cover any and all modifications and forms which may come within the language and scope of the appended claims.

What is claimed is:

1. Floating eyewear eyeglasses that fit snugly to a wearers head comprising, a frame, having a middle bridge therein with a pair of lenses, one on each side of the bridge, a pair of side temples, each having at least one opening therethrough, each side temple having an inside surface and an outside surface, said inside surface configured with a flat portion and an edge that protectively encompasses this flat portion, and the outside surface having an essentially convex outer shape, means to hinge each side temple to the frame permitting the side temples to be folded flat against the frame for ease of handling and storage, at least one resilient float pad configured in a recessed inverse image of the opening through each side temple, with each float pad forced into conformance with the temple opening securing the pad in place utilizing the pads flexibility, wherein said pads engagement with a wearers head creating a snug fit and said pad having sufficient buoyancy to overcome combined weight of the frame and temples permitting the eyewear to float in water with the temples protruding vertically above waters surface.

2. The floating eyeglasses as recited in claim 1 wherein said frame is a wrap around type with the lenses covering a wearers brow, cheekbone and a portion of a wearers temples.

3. The floating eyeglasses as recited in claim 1 wherein said frame is optically clear polycarbonate thermoplastic and said lenses are integrally formed with the frame.

4. The floating eyeglasses as recited in claim 1 wherein each side temple opening incorporates an internal perimeter in a sharp edge configuration.

5. The floating eyeglasses as recited in claim 1 wherein each side temple opening incorporates an internal perimeter in a half spherical edge configuration.

6. The floating eyeglasses as recited in claim 1 wherein each side temple opening incorporates an internal perimeter in a square edge configuration.

7. The floating eyeglasses as recited in claim 1 wherein said means to hinge each side temple to the eyewear frame are defined as a single gusseted knuckle integrally formed adjacent to each frame end and each side temple comprises a pair of aligned temple hinge knuckles each integral with the temple end such that each temple knuckle aligns on either side of said gusseted knuckle with a pin disposed through all of the knuckles permitting each temple to be pivotally attached to the frame.

8. The floating eyeglasses as recited in claim 1 wherein said float pads having an integral groove along a longitudinal axis, in reverse image of the edge of each temple opening, said pad contiguously engaging both the flat portion of the inside surface of each temple on one side and the temples outside surface on the other in a grommet like manner.

9. The floating eyeglasses as recited in claim 1 wherein said side temples further comprises, said at least one opening, defined as a front aperture and a rear aperture in each temple with the float pad having an interior and an exterior surface.

10. The floating eyeglasses as recited in claim 9 wherein said float pad is defined as a front float pad and a rear float pad, wherein each pads interior surface contiguously engaging the temples inside flat surface and the pads exterior surface contiguously engaging the temples outside surface adjacent to each opening in the temple.

11. The floating eyeglasses as recited in claim 9 wherein said float pad is defined as a front float pad and a rear float pad, wherein each pads interior surface contiguously engaging the temples inside flat surface, adjacent to each opening in the temple and the pads exterior surface contiguously engaging the temples outside surface, adjacent to each opening in the temple.

12. The floating eyeglasses as recited in claim 9 wherein said float pad is defined as a unitary float pad, wherein the interior surface of the pad contiguously engaging the temples inside flat surface and the pads exterior surface contiguously engaging the temples outside surface adjacent to each opening in the temple.

13. The floating eyeglasses as recited in claim 1 wherein said frame float pads further comprising a molded closed cell foam sponge.

14. The floating eyeglasses as recited in claim 13 wherein said frame float pad closed cell foam sponge has a density of from 11 pounds per cubic foot (176.2 kilograms per cubic meter) to 13 pounds per cubic foot (208.2 kilograms per cubic meter).

15. The floating eyeglasses as recited in claim 13 wherein said frame float pads closed cell foam sponge further comprising a bright visual color integrally molded therein so as to be easily discernible when the eyewear is floating in water.

16. The floating eyeglasses as recited in claim 13 wherein said frame float pads closed cell foam sponge further comprising an integrally molded color that matches the floating eyewear frame and temples for perceptible continuity.

17. The floating eyeglasses as recited in claim 1 wherein said temple float pads have a textured surface on a surface contiguous with a wearer for creating a non-slip grip.

18. The floating eyeglasses as recited in claim 1 further comprising a plurality of frame float pads formed of closed cell foam sponge attached to the frame adjacent to the means to hinge each side temple to the frame.

19. The Floating eyeglasses as recited in claim 18 wherein said temple float pads closed cell foam sponge is from 1 millimeter to 3 millimeters thick.

20. Floating eyeglasses that fit snugly to a wearers head comprising, a frame, having a pair of lenses therein, a pair of side temples, each having at least one opening therethrough, means to hinge each side temple to the frame permitting the side temples to be folded flat against the frame for ease of handling and storage, at least one resilient float pad forced into conformance with the temple opening securing the pad in place utilizing the pads flexibility, wherein said pads engagement with a wearers head creating a snug fit and said pad having sufficient buoyancy to overcome combined weight of the frame and temples permitting the eyewear to float in water with the temples protruding vertically above waters surface.

* * * * *